United States Patent [19]

Tomiyama

[11] Patent Number: 4,564,678

[45] Date of Patent: Jan. 14, 1986

[54] SUBSTITUTED AMINOTHIAZOLES AND METHOD OF MANUFACTURING THE SAME

[75] Inventor: Tsuyoshi Tomiyama, Sakaki, Japan

[73] Assignee: Kotobuki Seiyaku Company, Limited, Sakaki, Japan

[21] Appl. No.: 553,182

[22] Filed: Nov. 18, 1983

[30] Foreign Application Priority Data

Nov. 19, 1982 [JP] Japan ................................ 57-203432

[51] Int. Cl.$^4$ .................... A61K 31/495; C07D 417/06
[52] U.S. Cl. ...................................... 544/367; 546/19; 546/209
[58] Field of Search ................... 544/367; 546/19, 209

[56] References Cited

U.S. PATENT DOCUMENTS 4,321,372 3/1982 Kadin .................................. 546/209
4,411,900 10/1983 Ueda et al. .......................... 544/367

FOREIGN PATENT DOCUMENTS 30092 6/1981 European Pat. Off. ............ 424/251

Primary Examiner—Marion C. McCamish
Assistant Examiner—S. A. Gibson
Attorney, Agent, or Firm—Robert E. Burns; Emmanuel J. Lobato; Bruce L. Adams

[57] ABSTRACT

A series of new thiazole derivatives are disclosed. These compounds have an outstanding anti-gastric secretion activity. The compounds of this invention can be obtained by reacting 4-halogenated-alkyl-thiazole with its corresponding piperidine derivative or piperazine derivative.

7 Claims, No Drawings

SUBSTITUTED AMINOTHIAZOLES AND METHOD OF MANUFACTURING THE SAME

SUMMARY OF THE INVENTION

The principal object of the present invention is the provision of novel compounds having anti-gastric secretion activities.

Another objects of the present invention are the provisions of new thiazole derivatives and a method for manufacture thereof.

These and other objects of the invention will become apparent from the following description.

DETAILED DESCRIPTION OF THE INVENTION

This invention relates to a series of new thiazole derivatives having anti-gastric secretion activity and procedures for manufacture thereof.

The new compounds of this invention are generally defined as formula I:

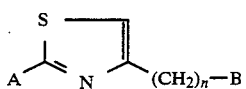

wherein A represents amino, acylamino, guanidino and N,N-di-lower alkyl-aminomethyleneamino group; n is an integer from 1 to 3; B represents

wherein Y is phenyl or substituted phenyl,

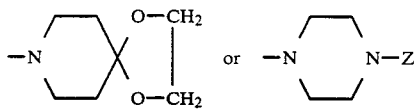

wherein Z is carboxy lower alkyl, and their non-toxic pharmacologically acceptable salts.

The term "lower alkyl" means alkyl groups which contain 1 to 3 carbon atoms, and also the "N,N-di-lower alkyl aminomethylene amino group" is represented by the formula:

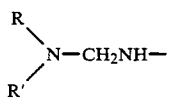

wherein R and R' each represents lower alkyl.

The compounds defined above of the present invention have an anti-histaminergic activity, especially, an outstanding gastric anti-secretory activity. These compounds can be administered in the form of free bases or pharmaceutically acceptable acid addition salts thereof, perorally or parenterally.

The following compounds relating to this invention are of particular interest.
(1) 2-amino-4-(4-hydroxy-4-phenylpiperidine-1-yl-methyl)thiazole
(2) 2-amino-4-(4-hydroxy-4-p-chlorophenyl-piperidine-1-yl-methyl)thiazole
(3) 2-acetylamino-4-(4-hydroxy-4-phenylpiperidine-1-yl-methyl)thiazole hydrochloride
(4) 2-acetylamino-4-(4-hydroxy-4-p-chlorophenyl-piperidino-1-yl-methyl)-thiazole
(5) 2-acetylamino-4-(4-hydroxy-4-phenylpiperidine-1-yl-ethyl)-thiazole
(6) 2-acetylamino-4-(4-hydroxy-4-p-chlorophenyl-piperidine-1-yl-ethyl)-thiazole
(7) 2-acetylamino-4-(4-hydroxy-4-phenylpiperidine-1-yl-propyl)-thiazole
(8) 2-acetylamino-4-(4-hydroxy-4-p-chlorophenyl-piperidine-1-yl-propyl)-thiazole
(9) 2-guanidino-4-(4-hydroxy-4-phenylpiperidine-1-yl-methyl)-thiazole
(10) 2-guanidino-4-(4-hydroxy-4-p-chlorophenylpiperidine-1-yl-methyl)-thiazole
(11) 2-propionylamino-4-(4-hydroxy-4-phenylpiperidine-1-yl-methyl)-thiazole hydrochloride
(12) 2-propionylamino-4-(4-hydroxy-4-p-chlorophenyl-piperidine-1-yl-methyl)-thiazole hydrochloride
(13) 2-(N,N-dimethylaminomethyleneamino)-4-(4-hydroxy-4-phenylpiperidine-1-yl-methyl)-thiazole hydrochloride
(14) 2-(N,N-dimethylaminomethyleneamino)-4-(4-hydroxy-4-p-chlorophenylpiperidine-1-yl-methyl)-thiazole hydrochloride
(15) 2-(N,N-dimethylaminomethyleneamino)-4-(4-hydroxy-4-phenylpiperidine-1-yl-methyl)-thiazole hydrochloride
(16) 2-(N,N-diethylaminomethyleneamine)-4-(4-hydroxy-4-p-chlorophenylpiperidine-1-yl-methyl)-thiazole hydrochloride
(17) 2-(N,N-dimethylaminomethyleneamino)-4-(4-carboxyethylpiperazine-1-yl-methyl)-thiazole hydrochloride
(18) 2-(N,N-dimethylaminomethyleneamino)-4-(4,4-ethylenedioxypiperidine-1-yl-methyl)-thiazole hydrochloride The above-mentioned compounds numbered from 1 to 18, will be referred to hereinafter, as Compound 1, Compound 2, . . . , Compound 18, respectively.

The new compounds of the present invention of the general formula I can be prepared in the following manner:

Compounds of general formula II:

$$\underset{A}{\overset{S}{\diagdown}}\underset{N}{\diagup}\underset{(CH_2)_n-X}{} \quad (II)$$

wherein X is halogen atom and, A and n are as defined above, are reacted with compounds of general formula III:

$$H-B \quad (III)$$

wherein B is as defined before.), in the presence of a base such as sodium methoxide, sodium ethoxide or potassium carbonate in ethylacetate, tetrahydrofuran or dimethylformamide. The reaction can be carried out at room temperature, but heating of the reaction mixture is desirable. 2-Amino-4-chloromethylthiazole, which has NH₂ for symbol A and Cl for X in formula II is obtained by condensation of thiourea with 1,3-dichloroacetone. In case n is 2 and 3, 3-chloropropionyl chloride and 4-chlorobutyryl chloride are reacted with diazomethane or more easily with trimethyl silyldiazomethane (Shioiri: Chem. Pharm. Bull. 29,(11) 3249 1981) to give 1,4-dichloro-2-butanone and 1,5-dichloro-2-pentanone respectively, which are subsequently condensed with thiourea to give the required compound.

The acylation of NH$_2$ group in position 2 is carried out by the conventional procedure.

The amino group of 2-amino-4-chloroalkyl-thiazole is converted to N,N-di-lower alkyl-aminomethyleneamino group with the Vilsmeier reagent which is obtained by reacting dimethylformamide or diethylformamide with thionyl chloride or phosphorus oxychloride according to G. R. Pettit (Can. J. Chem. 43, 2640 '65) and V. Krchnal (Coll. Czecho. Chem. Comm. 40, 1396,1975).

The compound of general formula III, in which B is

is obtained via substituted α-methylstyrene according to P. A. Janssen (J. Med. & Pharm. Chem., I, 281, '59).

The following examples will serve to illustrate the invention but are not to be construed to limit the scope of the invention.

EXAMPLE 1

Manufacture of Compound 1

A solution of 2-amino-4-chloromethylthiazole hydrochloride 0.93 g, 4-hydroxy-4-phenylpiperidine 0.44 g and potassium carbonate 1.38 g in ethyl acetate 020 ml is refluxed overnight. After cooling to room temperature, the reaction mixture is filtered off. The filtrate is washed with water and dried over sodium sulfonate and then the solvent is evaporated under reduced pressure. The residue is recrystallized in ethanol using a small amount of activated carbon, to give 0.1 g of the required substance.

m.p.: 220°–223° C.
ir: 3400, 3280, 3170, 2940, 1620, 1520 cm$^{-1}$
M.S.(m/e): 289(M+)

EXAMPLE 2

Manufacture of Compound 2

Ten ml of anhydrous methanol is added to 0.23 g of sodium metal. To this solution is added 2-aminothiazole dropwise by cooling with ice-water. After adding p-chlorophenyl-4-hydroxypiperidine, the reaction mixture is refluxed overnight. After the reaction is completed, the reaction mixture is concentrated and 10 ml of water is added to it. The resulting mixture is subjected to ethyl acetate extraction. The solvent layer is dried over anhydrous sodium sulfonate and concentrated under reduced pressure. The residue is applied to silica-gel column chromatography, using ethyl acetate as the elute, to give 0.065 g of compound 2.

m.p.: 149°–150° C.
ir: 3810, 3040, 1440, 1200, 1130 cm$^{-1}$
M.S.: (m/e) 323 (M+)

EXAMPLE 3–12

The compounds 3 to 12 are obtained by reacting a compound shown in column I of Table I with a compound shown in column II of Table 1, according to Example 2 and converted to hydrochloride salts by the conventional procedure.

TABLE 1

| Example No. | I A | $-(CH_2)_n-X$ | II H—B |
|---|---|---|---|
| 3 | CH$_3$CONH— | —CH$_2$Cl | H—N piperidine with OH and phenyl |
| 4 | CH$_3$CONH— | —CH$_2$Cl | H—N piperidine with OH and 4-Cl-phenyl |
| 5 | CH$_3$CONH— | —CH$_2$CH$_2$Cl | H—N piperidine with OH and phenyl |
| 6 | CH$_3$CONH— | —CH$_2$CH$_2$Cl | H—N piperidine with OH and 4-Cl-phenyl |

TABLE 1-continued

Structure I: A-C(=S)-N=C(-(CH₂)ₙ-X)- (thiazoline-type) with -(CH2)n-X substituent
Structure II: H-B

| Example No. | A | -(CH₂)ₙ-X | H-B |
|---|---|---|---|
| 7 | CH₃CONH— | —CH₂CH₂CH₂Cl | H-N(piperidine)-C(OH)(phenyl) |
| 8 | CH₃CONH— | —CH₂CH₂CH₂Cl | H-N(piperidine)-C(OH)(4-chlorophenyl) |
| 9 | NH₂—C(=NH)—NH— | —CH₂Cl | H-N(piperidine)-C(OH)(phenyl) |
| 10 | NH₂—C(=NH)—NH— | —CH₂Cl | H-N(piperidine)-C(OH)(4-chlorophenyl) |
| 11 | CH₃CH₂CONH— | —CH₂Cl | H-N(piperidine)-C(OH)(phenyl) |
| 12 | CH₃CH₂CONH— | —CH₂Cl | H-N(piperidine)-C(OH)(4-chlorophenyl) |

EXAMPLE 3

Compound 3 m.p.: 81°–83° C.
ir: 3350, 3040, 2950, 2680, 1710, 1620, 1550 cm$^{-1}$
M.S. (m/e): 331 (M$^+$—HCl)

EXAMPLE 4

Compound 4 m.p.: 103°–106° C.
ir: 3200, 3050, 2700, 1630 cm$^{-1}$
M.S.(m/e): 365(M$^+$—HCl)

EXAMPLE 5

Compound 5 m.p.: 159°–161° C.
ir: 3800, 3140, 3025, 2800, 1640, 1550 cm$^{-1}$
M.S. (m/e): 345 (M$^+$+1)

EXAMPLE 6

Compound 6 m.p.: 199°–201° C.
ir: 3140, 3025, 2925, 2900, 2800, 1640, 1550 cm$^{-1}$
M.S.(m/e): 380 (M$^+$—1)

EXAMPLE 7

Compound 7 m.p.: 117°–118° C.
ir: 3900, 3220, 2930, 2900, 1640, 1580 cm$^{-1}$

EXAMPLE 8

Compound 8 m.p.: 140°–142° C.
ir: 3840, 3300, 3100, 1580, 1500, 1470 cm$^{-1}$

EXAMPLE 9

Compound 9 m.p.: 137°–139° C.

ir: 3350, 3150, 2900, 2810, 1640, 1600, 1550, 1490 cm$^{-1}$
M.S. (m/e): 331 (M$^+$)

EXAMPLE 10

Compound 10 m.p.: 137°–139° C.
ir: 3350, 3150, 2930, 2820, 1640, 1600, 1550, 1485 cm$^{-1}$
M.S. (m/e) 366 (M$^+$ −1)

EXAMPLE 11

Compound 11 m.p.: 80°–83° C.
ir: 3200, 2700, 1630, 1440 cm$^{-1}$

EXAMPLE 12

Compound 12 m.p.: 80°–83° C.
ir: 3250, 2700, 1630 cm$^{-1}$

EXAMPLE 13

2-(N,N-dimethylaminomethyleneamino)-4-(4-hydroxy-4-phenylpiperidine-1-yl-methyl)thiazole hydrochloride (Compound 13)

Step I . . .
2-(N,N-dimethylaminomethyleneamino)-4-chloromethyl-thiazole

To an ice-water cooled solution of 8.77 g of dimethylformamide in 35 ml of tetrahydrofuran is added 9.20 g of phosphorus oxychloride in tetrahydrofuran 21 ml dropwise for 30 minutes. The reaction mixture is stirred for 30 minutes at room temperature and then 7.4 g of 2-amino-4-chloromethylthiazole in 28 ml of the same solvent is added. After continuous stirring overnight, the reaction mixture is added 20 ml of water and the resulting solution is alkalinized. After extraction with chloroform, the organic phase is washed with saturated sodium chloride solution, dried over magnesium sulfonate and evaporated. The residue is solidified by standing at room temperature.
ir: 3040, 1620, 1505, 1470, 1435, 1410 cm$^{-1}$
M.S.: (m/e) 204 (M$^+$)

Step II . . . Compound 13

To a solution of 0.075 g of sodium in 7 ml of anhydrous ethanol are added 0.29 g of 4-hydroxy-4-phenylpiperidine and 0.67 g of 2-(N,N-dimethylaminomethylene amino)-4-chloromethyl thiazole (the final product of step I). The resulting mixture is refluxed for 5 hours and evaporated. After adding 15 ml of water, the solution is subjected to ethyl acetate extraction. Then the organic phase is washed with water, dried over sodium sulfate and the organic solvent is removed. The residue is fractionated by silica-gel column chromatography using ethyl acetate:ethanol (1:1) solution as eluent to give 0.21 g of a free base product. The product is converted to HCl salt and recrystallized with ether-ethanol solution.
m.p.: 190°–192° C.
ir: 3320, 3050, 2925, 2720, 1690, 1530 cm$^{-1}$
M.S.: (m/e) 344 (M$^+$ −HCl)

EXAMPLE 14–18

Compounds from 14 to 18 are obtained by reacting compounds shown in column I of Table 2 with compounds in column II according to the procedure of example 13.

TABLE 2

| Example No. | I A | −(CH$_2$)$_n$−X | II H−B |
|---|---|---|---|
| 14 | (CH$_3$)$_2$NCH$_2$NH− | −CH$_2$Cl | H−N piperidine with OH and 4-Cl-phenyl |
| 15 | (CH$_3$CH$_2$)$_2$NCH$_2$NH− | −CH$_2$Cl | H−N piperidine with OH and phenyl |
| 16 | (CH$_3$CH$_2$)$_2$NCH$_2$NH− | −CH$_2$Cl | H−N piperidine with OH and 4-Cl-phenyl |
| 17 | (CH$_3$)$_2$NCH$_2$NH− | −CH$_2$Cl | H−N piperazine−CH$_2$CH$_2$COOH |

TABLE 2-continued

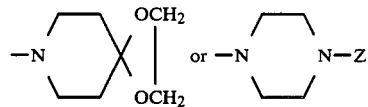

| Example No. | A | (CH₂)ₙ—X<br>—(CH₂)ₙ—X | II<br>H—B |
|---|---|---|---|
| 18 | (CH₃)₂NCH₂NH— | —CH₂Cl | 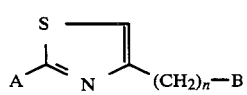 |

EXAMPLE 14

Compound 14 m.p.: 185°–187° C.
ir: 3360, 3060, 2930, 2700, 1690, 1640 cm⁻¹
M.S.: (m/e) 378 (M⁺−HCl)

EXAMPLE 15

Compound 15 m.p.: 170°–172° C.
ir: 3350, 2950, 2690, 1675, 1535, 1505 cm⁻¹
M.S.: (m/e) 373 (M⁺−HCl)

EXAMPLE 16

Compound 16 m.p.: 197°–199° C.
ir: 3270, 2910, 2650, 1670, 1540 cm⁻¹
M.S.: (m/e) 407 (M⁺−HCl)

EXAMPLE 17

Compound 17 m.p.: 212°–214° C.
ir: 2950, 1690, 1535 cm⁻¹
M.S.: (m/e) 325 (M⁺−HCl)

EXAMPLE 18

Compound 18 m.p.: 171°–172° C.
ir: 2950, 2820, 2680, 2530, 1685, 1540 cm⁻¹
M.S.: (m/e) 310 (M⁺+1−HCl)

What is claimed is:

1. A thiazole compound of the formula

wherein:
A is an amino, acylamino, guanidino or N,N-di-lower alkylaminomethyleneamino group;
n is an integer from 1 to 3;
B is

wherein Y is a phenyl or chloro-substituted phenyl group,

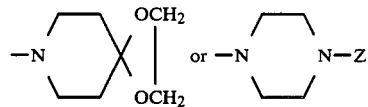

wherein Z is carboxy lower alkyl group,
and pharmaceutically acceptable acid addition salts thereof.

2. The compound according to claim 1 wherein A represents the amino group and B represents

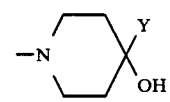

wherein Y is as defined in claim 1.

3. The compound according to claim 1 wherein A represents the acylamino group and B represents

4. The compound according to claim 1 wherein A represents the N,N-di-lower alkyl-aminomethyleneamino group and B represents

wherein Y is as defined in claim 1.

5. The compound according to claim 1 wherein A represents the guanidino group and B represents

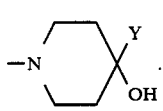

6. The compound according to claim 1 wherein B represents

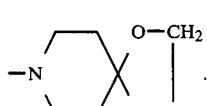

7. The compound according to claim 1 wherein B represents
wherein Z is as defined in claim 1.
* * * * *